(12) United States Patent
Joshi

(10) Patent No.: US 8,252,026 B2
(45) Date of Patent: Aug. 28, 2012

(54) SPINAL IMPLANT FOR FACET JOINT

(75) Inventor: Abhijeet B. Joshi, Austin, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 827 days.

(21) Appl. No.: 11/677,427

(22) Filed: Feb. 21, 2007

(65) Prior Publication Data
US 2008/0234735 A1 Sep. 25, 2008

(51) Int. Cl.
*A61B 17/70* (2006.01)

(52) U.S. Cl. ......... 606/247; 606/246; 606/248; 606/249

(58) Field of Classification Search .......... 606/246–248, 606/250–253; 623/17.11–17.16
See application file for complete search history.

(56) References Cited

U.S. PATENT DOCUMENTS

| | | | |
|---|---|---|---|
| 4,763,644 A | 8/1988 | Webb | |
| 4,805,602 A | 2/1989 | Puno et al. | |
| 4,887,596 A | 12/1989 | Sherman | |
| 4,950,269 A | 8/1990 | Gaines et al. | |
| 5,129,388 A | 7/1992 | Vignaud et al. | |
| 7,250,052 B2 | 7/2007 | Landry et al. | |
| 7,708,765 B2* | 5/2010 | Carl et al. | 606/279 |
| 7,837,711 B2* | 11/2010 | Bruneau et al. | 606/246 |
| 2003/0028250 A1* | 2/2003 | Reiley et al. | 623/17.11 |
| 2003/0040746 A1* | 2/2003 | Mitchell et al. | 606/61 |
| 2005/0033434 A1* | 2/2005 | Berry | 623/17.14 |
| 2006/0036246 A1* | 2/2006 | Carl et al. | 606/61 |

OTHER PUBLICATIONS

U.S. Appl. No. 10/698,010, filed Oct. 30, 2003, Landry, et al.
U.S. Appl. No. 10/698,049, filed Oct. 30, 2003, Landry, et al.
U.S. Appl. No. 11/234,706, filed Nov. 23, 2005, Robert Jones, et al.

* cited by examiner

*Primary Examiner* — Eduardo C Robert
*Assistant Examiner* — Christina Negrelli
(74) *Attorney, Agent, or Firm* — Seager Tufte & Wickhem LLC

(57) ABSTRACT

An apparatus (10) and method are provided for supporting an adjacent pair of vertebra (14, 16) relative to each other by anchoring a support frame (30) to the superior spinous process (24) and the inferior spinous process (28) of two adjacent vertebra (14, 16); and anchoring the support frame (30) to either the superior facets (34) or inferior facets (32) of the two adjacent vertebrae (14, 16).

20 Claims, 2 Drawing Sheets

US 8,252,026 B2

SPINAL IMPLANT FOR FACET JOINT

CROSS-REFERENCE TO RELATED APPLICATIONS

Not Applicable.

FEDERALLY SPONSORED RESEARCH OR DEVELOPMENT

Not Applicable.

MICROFICHE/COPYRIGHT REFERENCE

Not Applicable.

FIELD OF THE INVENTION

The present invention generally relates to spinal implant systems and the like, and in more particular applications, to implant that connect adjacent vertebrae for correction, fixation, and/or stabilization of a human spine.

BACKGROUND OF THE INVENTION

Lower back pain is often associated with disc degenerative disease. Often, disc degeneration and facet degeneration occur simultaneously, with one being the cause and the other the effect. Disc degeneration leads to disc height loss altering the normal spinal biomechanics and motion, including abnormal loading of the facet joints. The nerve fibers in the facet joints can be a source of scintillating pain as a result of the compressive or abnormal loading of the facet joints. While there are a number of procedures (such as spinal fusion, artificial discs, and artificial facet joints) directed towards alleviating the conditions associated with disc degeneration and/or facet degeneration, there is a continuing desire for improved methods and apparatus.

SUMMARY OF THE INVENTION

In accordance with one feature of the invention, a spinal implant is provided for reducing abnormal loading in the facet joints of an adjacent pair of vertebras. The implant includes a frame sized to extend between two adjacent vertebrae on the posterior side of a spine. The frame includes a first anchor point configured to be anchored to the spinous process of one of the vertebra, a second anchor point spaced longitudinally from the first anchor point and configured to be anchored to the spinous process of the other vertebra, a third anchor point spaced laterally from the first and second anchor points and configured to be anchored to a facet of one of vertebra, and a fourth anchor point spaced laterally opposite from the third anchor point and configured to be anchored to another facet of the one of the vertebra.

As one feature, each of the first and second anchor points includes a U-shaped opening configured to receive a spinous process, and the U-shaped opening is defined by a pair of projections that are spaced from each other to lie on opposite sides of a spinous process, with each of the projections having an apertures therein to receive a fastener that will pass through a spinous process received in the U-shaped opening.

In one feature, the frame further includes a longitudinal link extending between the first and second anchor points, a first cantilevered arm extending between the link and the third anchor point, and a second cantilevered arm extending between the link and the fourth anchor point.

According to one feature, each of the third and fourth anchor points includes a surface shaped to conform to the corresponding facet.

As one feature, the third anchor point includes an aperture formed in the first cantilevered arm to receive a fastener that engages the one of the vertebra, and the fourth anchor point includes an aperture formed in the second cantilevered arm to receive a fastener that engages the one of the vertebra.

In one feature, the longitudinal link has a bending stiffness selected to allow a desired range of motion for the spine.

According to one feature, each of the arms has a bending stiffness selected to allow a desired range of motion for the spine.

As one feature, the frame is a unitary component.

In one feature, the cantilevered arms are made from a different material than the material of the link and are detachably connected to the link.

As a further feature, each of the cantilevered arms includes a threaded end that is threaded into a corresponding receiving opening in the link.

In a further feature, each of the cantilevered arms includes an end that is press fit into a corresponding receiving opening in the link.

In accordance with one form of the invention, a method is provided for supporting an adjacent pair of vertebra relative to each other. The method includes the steps of: a) anchoring a support frame to the superior spinous process and the inferior spinous process of two adjacent vertebrae; and b) anchoring the support frame to either the superior facets or inferior facets of the two adjacent vertebral bodies.

As one feature, step a) is performed through a first incision; and step b) is performed through a pair of incisions spaced on laterally opposite sides of the first incision.

In one feature, step b) further includes assembling at least part of the support frame in situ.

According to one feature, steps a) and b) are performed through a common incision.

As one feature, step b) includes engaging a bone fastener with the frame and with at least one of the vertebral body, a superior facet, and an inferior facet.

In accordance with one feature of the invention, a method is provided for supporting an adjacent pair of vertebra relative to each other. The method includes the steps of: controlling the spacing between a superior spinous process and an inferior spinous process of two adjacent vertebrae; and providing cantilever support to the facet joints of two adjacent vertebras from the superior spinous process and the inferior spinous process of the two adjacent vertebras.

As one feature, the controlling step includes connecting a link to the superior spinous process and the inferior spinous process.

In one feature, the providing step includes connecting a pair of arms to the link, each of the arms extending from the link to one of the facet joints.

According to one feature, the providing step further includes inserting the arms through a respective pair of incisions prior to the connecting step.

Other objects, features, and advantages of the invention will become apparent from a review of the entire specification, including the appended claims and drawings.

DETAILED DESCRIPTION OF THE PREFERRED EMBODIMENT

Figure 1:
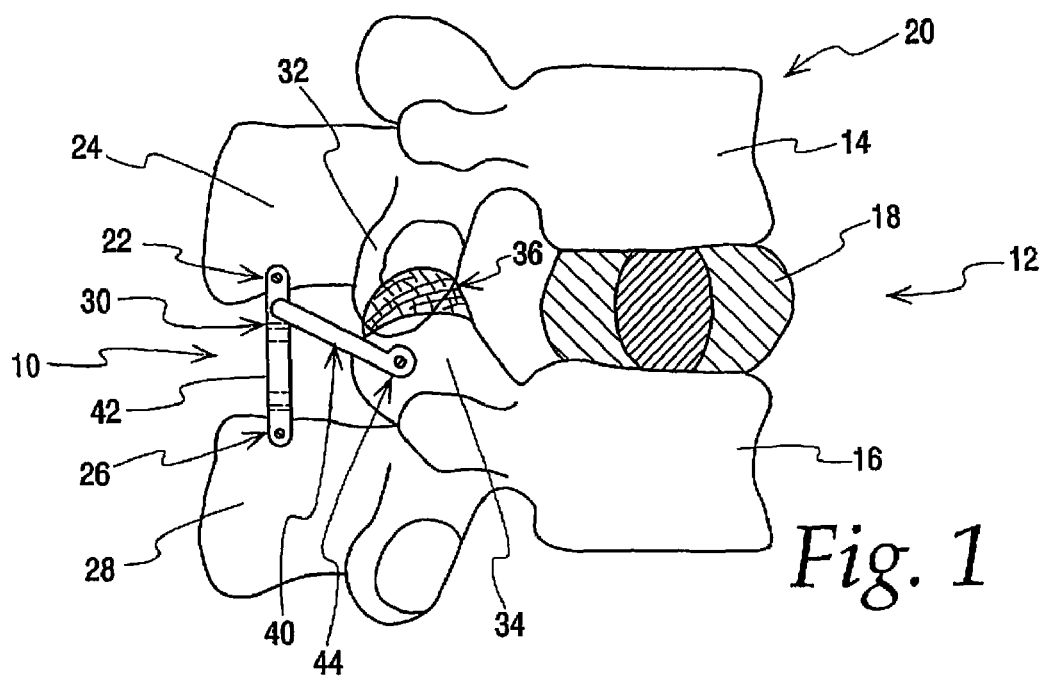
FIG. 1 is a somewhat diagrammatic side view of a portion of a spine incorporating the invention.

With reference to FIG. 1, an implant is shown diagrammatically at 10 in connection with a pair 12 of adjacent superior and inferior vertebrae 14 and 16, respectively, and a corresponding disc 18 of a spinal column 20. The implant 10 includes an anchor point 22 anchored to the superior spinous process 24, an anchor point 26 anchored to inferior spinous process 28, and a structure or frame 30 extending between the anchor points 22 and 26 to support the spinous processes 24 and 28 with respect to each other. More specifically, the frame 30 of the implant 10 serves to increase the distance between the spinous processes 24 and 28, which in turn "lifts" the inferior facets (inferior articular processes) 32 (only one shown in FIG. 1) of the superior vertebra 14 relative to the superior facets (superior articular process) 34 (only one shown in FIG. 1) of the inferior vertebra 16 to help alleviate pain resulting from abnormal or compressive loading of the facet joints 36 (only one shown in FIG. 1). In this regard, it may be desirable in some applications to make the vertical portion of the frame 30 adjustable so as to increase or decrease it height in the vertical direction depending upon the desired separation distance between the adjacent spinous processes 24 and 28. Any suitable structure, such as a mating screw thread or ratchet type mechanism, can be included as part of the frame 30 to accomplish this height adjustment.

Preferably, the frame 30 also includes a pair of facet supports or arms 40 (only one shown in FIG. 1), with each arm 40 being cantilevered from a central structure 42 of the frame 30 and extending to an anchor point 44 that is configured to anchor the arm to one of the facets 32 or 34. The arms 40 serve to stabilize the spine 20, particularly for lateral motion, and to further reduce compressive or abnormal loading of the facet joints 36 by reacting loads from one vertebra 14, 16 to the other vertebra 14, 16 through the frame 30, particularly loads resulting from lateral flexion/reduction (abduction) of the spine and from spinal rotation. Because the arms 40 can react such loads, they also allow for one or both sets of facets 32, 34 to be modified or even amputated as indicated by the particular procedure and/or spinal condition.

Figure 2:
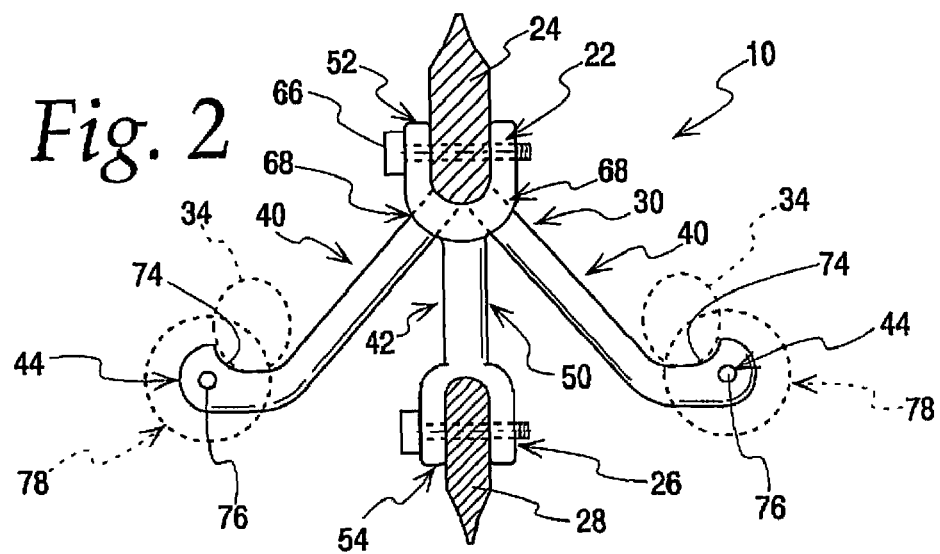
FIG. 2 is a somewhat diagrammatic posterior view of a portion of a spine incorporating one embodiment of the invention.
Figure 3:
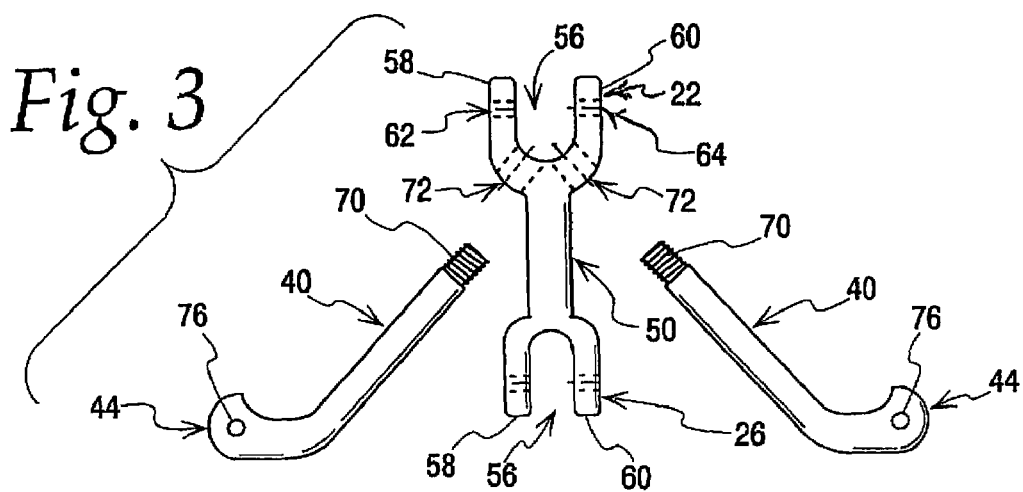
FIG. 3 is an exploded view of the embodiment of FIG. 2.

FIGS. 2 and 3 show an embodiment of the implant 10 wherein the central structure 42 of the frame 30 is provided in the form of a longitudinal link 50 that forms a knuckle joint 52 with the spinous process 24 at the anchor point 22 and a knuckle joint 54 with the spinous process 28 at the anchor point 26. More specifically, as best seen in FIG. 3, at each of the anchor points 22 and 26, the link 50 includes a U-shaped opening 56 defined by a pair of projections 58 and 60 that are spaced from each other to lie on opposite sides of the corresponding spinous process 24, 28 that is received in the U-shaped opening 56. Each of the projections 58 and 60 has a transverse or lateral aperture or bore 62 and 64, respectively, to receive a fastener 66 that extends through the corresponding spinous process 24, 28 that is received in the U-shaped opening 56. The fastener 66 can be of any suitable type. For example, the fastener 66 could be in the form of a shoulder bolt or screw that has threaded end that is received in corresponding internal threads formed in one of the apertures 62, 64, with a smooth cylindrical shaft of the bolt extending through the corresponding spinous process 24, 28. As another example, the fastener 66 could be a bone screw or anchor that is threaded through the corresponding spinous process 24, 28, with the apertures 62, 64 either being unthreaded or threaded to receive the bone screw or anchor. It should be appreciated that there are many other possible configurations for the fastener 66.

In the embodiment of FIGS. 2 and 3, the arms 40 are separate pieces from the link 50 and are each detachably connected to the link 50 at a connection joint 68 with a suitable connection, one example of which is shown in FIG. 3 wherein the ends 70 of the arms 40 have external threads that are received in corresponding threaded opening 72 in the link 50. As another example, the ends 70 of the arms could be press fit into unthreaded openings 72 in the link 50. Preferably, as best seen in FIG. 2, the anchor point 44 of each arm 40 includes at least one surface 74 that is shaped to conform to the corresponding facet 32, 34. Each of the anchor points 44 includes a bore or aperture 76 that can receive a suitable bone fastener 78 (shown diagrammatically in phantom in FIG. 2) that engages the vertebra 14, 16 of the corresponding facet 32, 34 to anchor the anchor point 44 to the corresponding facet 32, 34. In this regard, the bone fastener 78 may engage the vertebral body, a superior facet, or an inferior facet, and, while the apertures 76 are shown extending through the anchor points 44 along a posterior/anterior axis, each aperture 76 may be formed through the anchor point 44 extending along a lateral axis, or at any other angle/orientation that may be required to allow the bone fastener 78 to engage the intended portion of the corresponding vertebra 14, 16.

Preferably, the bending stiffness of the link 50 and the bending stiffness of each of the arms 40 is selected to allow a desired range of motion (ROM) for the spine 20 and the vertebrae 14, 16. For some applications, such as spinal fusion, little or no ROM will be desired, so it will be desirable to select bending stiffness that make the frame 30 essentially rigid. On the other hand, in some applications where dynamic stabilization is desired, the bending stiffness will be selected to make the frame more compliant. For example, in some embodiments it may be desirable to select a bending stiffness for the link 50 that will allow in the range of $\pm 1°$ to $\pm 7°$ of flexion/extension spinal motion, and for the bending stiffness of the arms 40 to allow $\pm 2°$ to $\pm 5°$ of lateral flexion/reduction spinal motion. Those skilled in the art will understand that there are many possible ways to obtain a desired bending stiffness for the link 50 or arms 40, including material selection and design of the cross sections for the link 50 and arms 40. In this regard, in some embodiments it may be desirable to make the arms 40 from a different material than the material used for the link 50. The arms 40 and link 50 may be formed of any suitable biocompatible material, including suitable metals, polymers, ceramics, inorganic compositions, and combinations thereof. It will also be appreciated that the cantilever construction of the arms 40 tends to inherently provide a lower bending stiffness that what will be provided by the link 50. Further discussion on possible ways to obtain a desired bending stiffness in a member such as the link 50 or arms 40 is disclosed in co-pending application Ser. No. 11/564,930, filed on Nov. 30, 2006, entitled "Apparatus and Methods for Spinal Implants", the entire disclosure of which is incorporated herein by reference.

Figure 4:
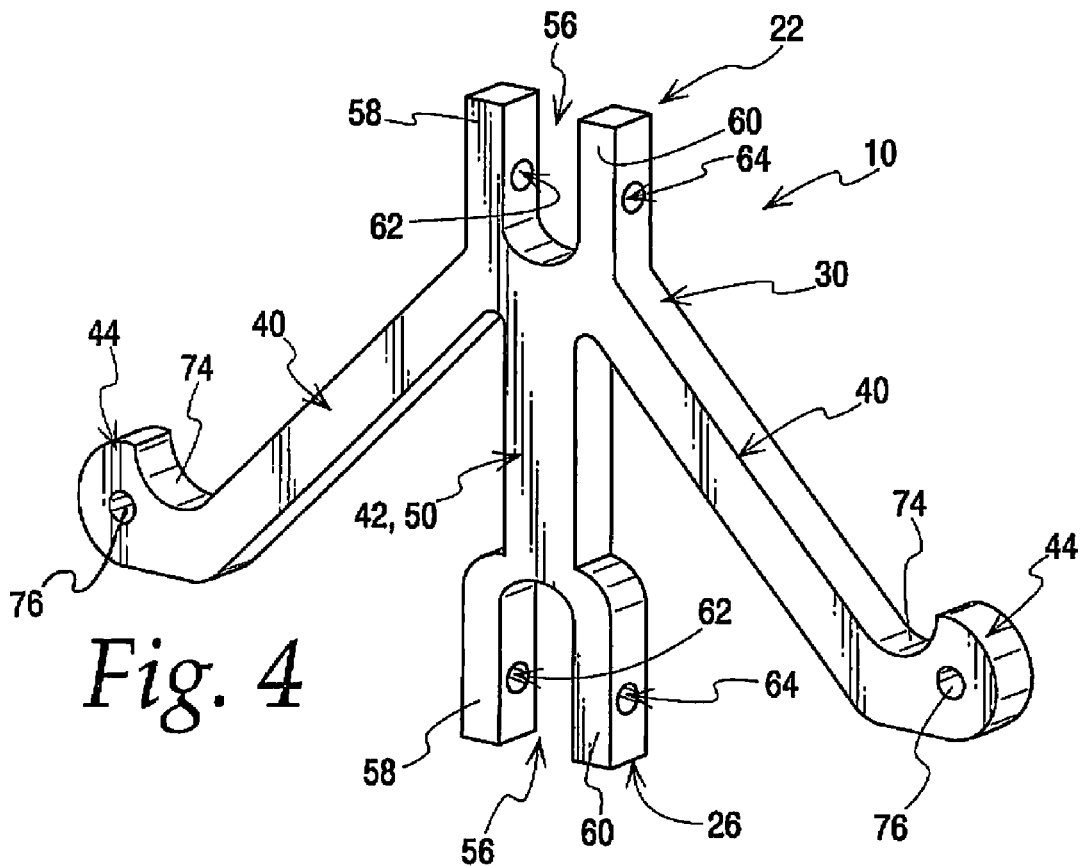
FIG. 4 is a perspective view of another embodiment of the invention.
Figure 5:
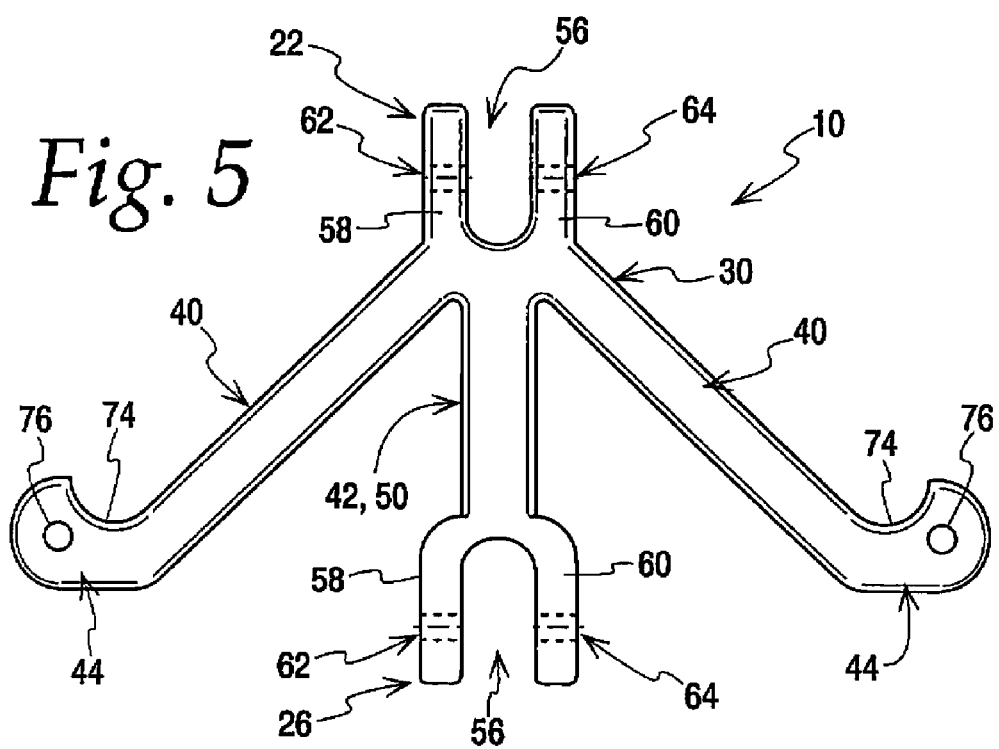
FIG. 5 is a plan view of the embodiment of FIG. 4.

FIGS. 4 and 5 illustrate another embodiment of the implant 10 wherein the frame 30 is a unitary component with the central structure/link 42/50 and the arms 40 are all made from the same material. Furthermore, the arms 40 have a rectangular cross section, rather than the circular cross section of the arms 40 in the embodiment of FIGS. 2 and 3. Given the examples of FIGS. 2-3 and FIGS. 4-5, it should be understood that there are many possible configurations for the central structure/link 42/50 and arms 40, including cross sections that are rectangular, circular, triangular, oval, T-shaped, I-beam shaped, helicoidal, elliptical, etc.

The implant 10 according to the invention may be used in minimally invasive surgery/less invasive surgery (MIS/LIS) or closed procedures or in non-MIS or open procedures, as desired, and as persons of ordinary skill in the art who have the benefit of the description of the invention understand. While the implant 10 of FIGS. 2-3 can be used with any surgical procedure, it is particularly suited for use with MIS Procedures. MIS procedures seek to reduce cutting, bleeding, and tissue damage or disturbance associated with implanting a spinal implant in a patient's body.

In an MIS procedure using the embodiment of FIGS. 2-3, the link 50 can be inserted through a small incision along the length of the spine 20, with custom tooling being used to install the fasteners 66 to connect the each of the anchor points 22 and 26 to the corresponding spinous process 24, 28. Each of the arms 40 can be inserted and attached to the link 50 through the same small punctures or incisions that will be used to install the bone fastener 78.

It will be understood by one skilled in the art that each particular procedure may require that the spinous processes 24, 28 and facets 32, 34 undergo certain preparations before the implant 10 is installed. For example, amputation and/or preparation of one or more of the facets 32, 34 has already been discussed. As a further example, it may be necessary to remove ligaments and/or to shape one or more of the spinous processes 24, 28 and facets 32, 34.

While the implant 10 is shown with a pair of facet supports or arms 40, each extending to an anchor point 44, in some procedures it may be desirable for the implant 10 to include only a single one of the arms 40 extending to a single anchor point 44 to one of the facets 32 or 34.

It should be understood that while the implant 10 has been disclosed herein in connection with a single pair 12 of adjacent superior and inferior vertebrae 14 and 16, the implant 10 can be done on multiple levels of adjacent vertebrae pairs 12. For example, a pair of implants 10 could be used with the anchor point 22 of one of the implants 10 and the anchor point 26 of the other implant 10 being anchored to the spinous process of the middle vertebrae of a group of three adjacent vertebrae. In this regard, the U-shaped openings 56 that are attached to the spinous process of the middle vertebrae could be sized so that they are attached to different parts of the spinous process with separate fasteners 66, or could be sized so that one of the openings 56 overlays the other opening 56 with a common fastener 66 that is received in both of the U-shaped openings 56.

It should be appreciated that the implant 10 as disclosed herein can provide either fixation or dynamic stabilization of a spine, and can help to provide a more natural load sharing between the intervertebral disc 18 and the posterior elements of the vertebrae 14, 16, including the facet joints 36. In this regard, the implants 10 may help to preserve and/or restore the intended function of the articulating surfaces of the vertebrae 14, 16.

The invention claimed is:

1. A spinal implant for use in connection with the facet joints of an adjacent pair of vertebrae, the implant comprising;
   a frame sized to extend between two immediately adjacent vertebrae on the posterior side of a spine, wherein the two immediately adjacent vertebrae are separated by a single intervertebral disc, the frame comprising:
   a single piece body having:
      a first anchor point having a first pair of projections extending from the single piece body, the first pair of projections defining a first U-shaped opening at a first end of the single piece body, the first anchor point being configured to be anchored to the spinous process of one of the two immediately adjacent vertebrae;
      a second anchor point having a second pair of projections extending from the single piece body, the second pair of projections defining a second U-shaped opening at a second end of the single piece body, the second anchor point extending longitudinally from the first anchor point and being configured to be anchored to the spinous process of the other one of the two immediately adjacent vertebrae, wherein each of the first and second U-shaped openings is configured to receive a spinous process; and
      a longitudinal link extending between the first and second anchor points;
   a third anchor point spaced laterally from the first and second anchor points and configured to be anchored to a facet of one of the two immediately adjacent vertebrae; and
   a first cantilevered arm extending between the longitudinal link and the third anchor point, wherein the first cantilevered arm includes an end configured to be received into a corresponding receiving opening in the longitudinal link.

2. The implant of claim 1 wherein each of the first and second pairs of projections comprises an aperture therein to receive a fastener passing through the spinous process received in the U-shaped opening.

3. The implant of claim 1 further comprising a fourth anchor point spaced laterally opposite from the third anchor point and configured to be anchored to another facet of the one of the two immediately adjacent vertebrae.

4. The implant of claim 3 wherein the frame further comprises:
   a second cantilevered arm extending between the longitudinal link and the fourth anchor point.

5. The implant of claim 4 wherein each of the third and fourth anchor points comprises a surface shaped to conform to the corresponding facet.

6. The implant of claim 4 wherein:
   the third anchor point comprises an aperture formed in the first cantilevered arm to receive a fastener that engages the one of the two immediately adjacent vertebrae; and
   the fourth anchor point comprises an aperture formed in the second cantilevered arm to receive a fastener that engages the one of the two immediately adjacent vertebrae.

7. The implant of claim 4 wherein the longitudinal link has a bending stiffness selected to allow a desired range of motion for the spine.

8. The implant of claim 4 wherein the longitudinal link has a bending stiffness selected to allow a desired range of motion for the spine and each of the arms have a bending stiffness selected to allow a desired range of motion for the spine.

9. The implant of claim 1 wherein the first cantilevered arm is made from a different material than the material of the longitudinal link and is detachably connected to the longitudinal link.

10. The implant of claim 1 wherein the end of the first cantilevered arm is configured to be threaded into the corresponding receiving opening in the longitudinal link.

11. The implant of claim 1 wherein the end of the first cantilevered arm is configured to press fit into the corresponding receiving opening in the longitudinal link.

12. A method of supporting an adjacent pair of vertebrae relative to each other, the method comprising the steps of:
  a) connecting the superior spinous process and the inferior spinous process of two immediately adjacent vertebrae via a first anchor point and a second anchor point of a body of a support frame, the body of the support frame being a single piece, the first anchor point having a first pair of projections extending from the body, the first pair of projections defining a first U-shaped opening at a first end of the body, the second anchor point having a second pair of projections extending from the body, the second pair of projections defining a second U-shaped opening at a second end of the body, the first anchor point and the second anchor point spaced longitudinally from each other via a longitudinal link, wherein each of the first and second U-shaped openings is configured to receive a spinous process, and wherein the two immediately adjacent vertebrae are separated by a single intervertebral disc; and
  b) anchoring the support frame to at least one facet of the two adjacent vertebrae via a third anchor point of the support frame, the third anchor point being spaced laterally from the first anchor point and the second anchor point at an end of a first cantilevered arm extending between the longitudinal link, the end of the first cantilevered arm being configured to be received into a corresponding receiving opening in the longitudinal link.

13. The method of claim 12 wherein step b) comprises anchoring the support frame to two of the facets of the two immediately adjacent vertebrae.

14. The method of claim 13 wherein:
  step a) is performed through a first incision; and
  step b) is performed through a pair of incisions spaced on laterally opposite sides of the first incision.

15. The method of claim 14 wherein step b) further comprises assembling at least part of the support frame in situ.

16. The method of claim 14 wherein steps a) and b) are performed through a common incision.

17. The method of claim 12 wherein step b) comprises engaging a bone fastener with the support frame and with at least one of the vertebral body, a superior facet, and an inferior facet.

18. A method of supporting an adjacent pair of vertebrae relative to each other, the method comprising the steps of:
  making an incision along a length of two immediately adjacent vertebrae, wherein the two immediately adjacent vertebrae are separated by a single intervertebral disc;
  inserting a link through the incision to control the spacing between a superior spinous process and an inferior spinous process of the two immediately adjacent vertebrae;
  anchoring a first anchor point of the link to the superior spinous process on an inferior vertebra of the two immediately adjacent vertebrae;
  anchoring a second anchor point of the link to the inferior spinous process on a superior vertebra of the two immediately adjacent vertebrae, the first anchor point and the second anchor point being on a single piece body of the link, thereby connecting the spinous processes of the two immediately adjacent vertebrae; and
  attaching at least an arm of the link to at least one facet joint of the two immediately adjacent vertebrae to reduce compressive or abnormal loading of facet joints of the two immediately adjacent vertebrae, wherein attaching at least an arm of the link to at least one facet joint of the two immediately adjacent vertebrae further comprises:
  inserting a pair of arms through a respective pair of incisions; and
  connecting the pair of arms to the link.

19. The method of claim 18 wherein the cantilevered arm of the link is detachably attached to the link.

20. The method of claim 18 wherein connecting the pair of arms to the link further comprises press fitting each of the arms into an opening in the link, extending the arm from the link to one of the facet joints.

* * * * *